US008982339B2

(12) United States Patent
Schönleber et al.

(10) Patent No.: US 8,982,339 B2
(45) Date of Patent: Mar. 17, 2015

(54) MATERIAL-WORKING DEVICE WITH IN-SITU MEASUREMENT OF THE WORKING DISTANCE (71) Applicant: Precitec Optronik GmbH, Neu-Isenburg (DE)

(72) Inventors: Martin Schönleber, Aschaffenburg (DE); Markus Kogel-Hollacher, Haibach (DE)

(73) Assignee: Precitec Optronik GmbH, Neu-Isenburg (DE)

( * ) Notice: Subject to any disclaimer, the term of this patent is extended or adjusted under 35 U.S.C. 154(b) by 0 days.

(21) Appl. No.: 13/667,809

(22) Filed: Nov. 2, 2012

(65) Prior Publication Data

US 2013/0120740 A1    May 16, 2013

Related U.S. Application Data (63) Continuation of application No. PCT/IB2011/052048, filed on May 10, 2011.

(30) Foreign Application Priority Data

May 10, 2010   (DE) .......................... 10 2010 016 862

(51) Int. Cl.
*G01B 11/14*     (2006.01)
*G01N 21/25*     (2006.01)
(Continued)

(52) U.S. Cl.
CPC ............ *G01N 21/255* (2013.01); *B23K 26/032* (2013.01); *B23K 26/048* (2013.01);
(Continued)

(58) Field of Classification Search
CPC ................. A61F 2009/00844; G01B 2290/70; G01B 11/14; G01B 7/023; G01B 11/026; B23K 26/032; B23K 26/048
USPC ...................... 356/497–498, 326, 72–73, 495
See application file for complete search history.

(56) References Cited

U.S. PATENT DOCUMENTS 6,099,522 A  *  8/2000  Knopp et al. .................... 606/10
6,396,069 B1 *  5/2002  MacPherson et al. ... 250/559.22
2002/0153500 A1 * 10/2002  Fordahl et al. ........... 250/559.29
(Continued)

FOREIGN PATENT DOCUMENTS

DE         102008049821       4/2010
EP             1977850         10/2008
WO           2011141867        11/2011

OTHER PUBLICATIONS

Schonleber; International Search Report and Written Opinion for serial No. PCT/IB2011/052048 filed May 10, 2011, mailed Sep. 21, 2011, 2 pgs.
(Continued)

Primary Examiner — Kara E Geisel
(74) Attorney, Agent, or Firm — Taylor English Duma LLP (57) ABSTRACT A material-working device with working beams of a beam generator and with in-situ measurement of a working distance between the beam generator and a workpiece, the material-working device including a working laser; a laser scanner for the working laser, the laser scanner including a two-dimensional deflecting device with scanner mirrors and a variable refocusing device at varying working distances; and a sensor device including a spectrometer and at least one sensor light source, wherein measuring beams together scan a working area of the workpiece by the laser scanner and an objective lens while gathering the working distance, and the measuring beams of at least two of the light sources of the sensor device being linearly polarized and being coupled into a working beam path of the laser scanner of the material-working device by an optical coupling element in a collimated state with crossed polarization directions.

17 Claims, 8 Drawing Sheets (51) Int. Cl.
 *B23K 26/03* (2006.01)
 *B23K 26/04* (2014.01)
 *B23K 26/08* (2014.01)
 *G01B 9/02* (2006.01)

(52) U.S. Cl.
 CPC ........ *B23K26/0807* (2013.01); *G01B 9/02007* (2013.01); *G01B 9/02044* (2013.01); *G01B 9/02091* (2013.01); *G01B 9/02063* (2013.01); *G01B 9/02036* (2013.01); *G01B 2290/70* (2013.01)
 USPC ............................................. 356/72; 356/498

(56) References Cited

U.S. PATENT DOCUMENTS

| | | | |
|---|---|---|---|
| 2003/0016353 A1* | 1/2003 | Detalle et al. | 356/318 |
| 2004/0021874 A1* | 2/2004 | Shimmick | 356/497 |
| 2005/0248771 A1* | 11/2005 | Eussen et al. | 356/498 |
| 2009/0273782 A1 | 11/2009 | Yoo et al. | |
| 2011/0180521 A1* | 7/2011 | Quitter et al. | 219/121.73 |

OTHER PUBLICATIONS

Schonleber; International Preliminary Report on Patentability for serial No. PCT/IB2011/052048 filed May 10, 2011, mailed Nov. 22, 2012, 7 pgs.

* cited by examiner

MATERIAL-WORKING DEVICE WITH IN-SITU MEASUREMENT OF THE WORKING DISTANCE

REFERENCE TO RELATED APPLICATIONS

This application is a continuation of International Application No. PCT/IB2011/052048, filed May 10, 2011, which claims priority to German Application No. 10 2010 016 862.9, filed May 10, 2010, both of which are hereby specifically incorporated by reference herein in their entireties.

TECHNICAL FIELD

The present disclosure relates to a material-working device with working beams of a beam generator and with in-situ measurement of the working distance between a beam generator and a workpiece.

SUMMARY

A material-working device with working beams of a beam generator and with in-situ measurement of a working distance between the beam generator and a workpiece, the material-working device comprising: a working laser; a laser scanner for the working laser, the laser scanner including a two-dimensional deflecting device with scanner mirrors and a variable refocusing device for varying working distances; an objective lens; and a sensor device including a spectrometer, at least two sensor light sources generating measuring beams, and an optical coupling element, wherein the measuring beams are linearly polarized in crossed polarization directions and collimated using the optical coupling element, and then directed to the workpiece through the laser scanner and the objective lens, and then directed back to the spectrometer to record to workpiece distance.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

FIG. 3 shows a raw spectrum (FIG. 3A) and a leveled spectrum (FIG. 3B) following working as disclosed.

FIG. 5 shows the polarisation- and angle-dependent transmission of scanner mirrors and specifically an angle of incidence of 57.5° in FIG. 5A, an angle of incidence of 45° in FIG. 5B and an angle of incidence of 27.5° in FIG. 5C.

DETAILED DESCRIPTION

The present disclosure relates to a material-working device with working beams of a beam generator and with in-situ measurement of the working distance between a beam generator and a workpiece and associated methods, systems, devices, and various apparatus relating thereto. It would be understood by one of skill in the art that the disclosed material-working device is described in but a few exemplary embodiments among many. No particular terminology or description should be considered limiting on the disclosure or the scope of any claims issuing therefrom.

The present disclosure relates to a material-working device with working beams of a beam generator and with in-situ measurement of the working distance between the beam generator and the workpiece. For this purpose the material-working device has a working laser with near-infrared working beams. A laser scanner comprising a two-dimensional deflecting device with scanner mirrors is arranged downstream of a working laser. An automatic refocusing device for varying working distances is provided.

Figure 8:
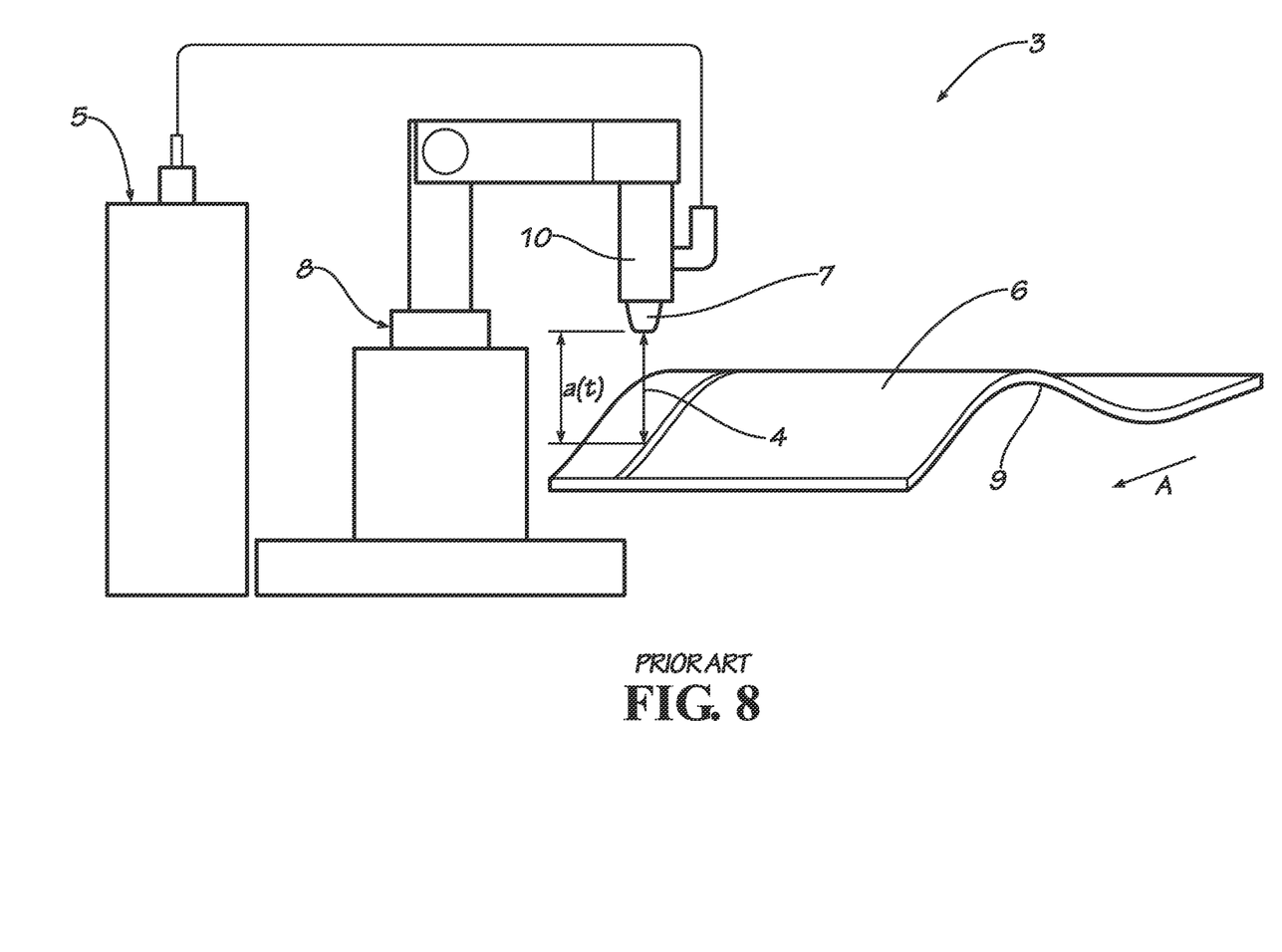
FIG. 8 shows a partially perspective principle drawing of a material-working device as disclosed in the prior art.

A material-working device of this type is known from EP 1 977 850 A1. FIG. 8 shows a partially perspective principle drawing of a material-working device 3 of this type in accordance with the prior art. This material-working device 3 works the slightly curved workpiece 6, shown in perspective, with working beams 4 of a beam generator 5 and with in-situ measurement of the working distance a between a working head 7 and the workpiece 6. For this purpose the material-working device 3 has a working laser with near-infrared working beams 4 as the beam generator 5. The working head 7 is guided by an industrial robot 8. An automatic refocusing device for time varying working distances a(t) is provided in the material-working device 3 to follow, for example, the curve 9 of the workpiece 6 when guiding the workpiece 6 in the direction of arrow A. To this end an optical coherence tomograph 10 for recording tomograms is provided in the working head 7.

One disadvantage of this material-working device 3 is that the measurement signals for tomogram recording are carried by optical fibres. In case of vibrations during operation oscillations in the optical fibres can modify spectral transmission and thus the polarisation state and the mix ratio between individual polarisation modes, thereby impairing the measurement result and so the tomogram recording.

The object of the present disclosure is to overcome the disadvantages of the prior art and to record the topography of a surface without touching it before, during and after working (ablation, deposition welding, etc.). The aim is to improve the reliability of control of the working process and the endpoint determination of material removal/deposition by means of distance measurement. A further object is to measure the distance from the workpiece to the working system absolutely, e.g., to refocus the laser. This object is achieved by means of the subject matter of the independent claims. Advantageous developments of the present disclosure are described in the dependent claims.

The present disclosure relates to a material-working device with working beams of a beam generator and with in-situ measurement of the working distance between the beam generator and the workpiece. For this purpose the material-working device has a working laser with working beams. A laser scanner comprising a two-dimensional deflecting device with scanner mirrors is arranged downstream of a working laser. An automatic refocusing device for varying working distances is provided. A sensor device comprising a spectrometer and at least two sensor light sources generates measuring beams which jointly sense the working area of the workpiece by means of the laser scanner and an objective lens while gathering the workpiece distance. The measuring beams of at least two of the sensor light sources are linearly polarised and coupled into the beam path of the laser scanner of the material-working device with crossed polarisation directions in a collimated state by an optical coupling element.

This material-working device has the advantage that a predetermined laser scanner optical assembly of a working laser is used as the sensor lens such that the working beam and sensor measuring beams are directed at the workpiece together by an F-theta objective lens system. The working laser provided is typically a solid-state laser with a wavelength range of 1030 nm to 1070 nm. A further advantage is that at least two sensor light sources generate the measuring beams which are linearly polarised and coupled into the beam path of the laser scanner of the material-working device with crossed polarisation directions in a collimated state by the laser scanner so as to afford the sensor device more robust protection from vibrations of the material-working device, especially since shaking and vibrations of the optical fibres used no longer impair the lighting and detecting properties thanks to the crossed polarisation directions. For this purpose a spectral-interferometric distance sensor (also referred to as an OCT or optical coherence tomograph) is integrated into the laser scanner in the material-working device for material working. To achieve its object the present disclosure thus proposes a combination of features which allow high quality distance measurement throughout the entire laser scanner volume. This is achieved primarily by means of spectral stabilisation measures.

The use of unpolarised light sources, preferably two light sources with linearly polarised beams split from the light sources and polarised by a polarising beam splitter and which are carried by a polarisation-maintaining fibre to a PBC (Polarisation Beam Combiner) and combined with crossed polarisation directions in the PBC by the polarising beam splitter, prevents any shaking of the optical fibres from modifying the polarisation state and thus the mix ratio between polarisation modes. Spectral transmission is therefore no longer impaired even when optical components have different spectral transmissions depending on polarisation direction.

If, however, there are different path differences in the two polarisation modes due to stress-induced birefringence or coating, for example, in the worst case scenario the distance peak splits into two sub-peaks. In such cases in a second embodiment of the present disclosure a birefringent element with main directions which correspond to the main directions of the polarisation-relevant components, such as the beam splitter and/or galvano mirror, is inserted into the beam path. This separates the two peaks to such an extent that a clean evaluation is possible.

Superluminescent diodes with linearly polarised beams are used as the light sources, these light sources being connected by polarisation-maintaining optical fibres to a polarisation beam coupler which combines the crossed polarisation directions by means of a polarising beam splitter. To couple the sensor beams into the working beam path in a collimated state a sensor beam path defined by the measuring beams has a narrow-band dichroic beam splitter such as a narrow-band notch filter.

Instead of a narrow-band dichroic beam splitter, it is also possible to provide a rotating filter wheel, which alternately couples laser light or sensor light into the laser scanner and rotates synchronously with a pulse frequency of the working laser, to couple the sensor beams into the working beam path in a collimated state such that the laser scanner is advantageously available for the measuring beam in the pulse pauses of the working laser and the working cycle is not impaired. In a further embodiment, it is also possible to couple the sensor beams into the working beam path in a collimated state by pivoting a deflecting mirror into the beam path.

The sensor light is preferably refocused using the focus tracking function of the laser. In this process the sensor light is coupled into the laser beam path in an almost collimated state. However, the lens of the sensor collimator is refocused to compensate for the chromatic focal spot shift of the F-theta objective lens system.

Despite the varying tilt of the dielectrically coated scanner mirrors it is possible to stabilise spectral reflectivity by setting a sensor wavelength close to the aforementioned laser wavelength of 1030 nm to 1070 nm at 1260 nm to 1360 nm (nanometers). A uniformly high tilt- and polarization-dependent scanner mirror reflectivity is thus also used for the sensor light.

In addition, it is possible to set the sensor wavelength within the scanner mirror "camera window" wavelength range at approx. 650 nm where the reflectivities of the scanner or galvano mirrors are also high and uniform. Commercial beam splitters for sensor beam coupling are available for this type of wavelength range. This arrangement simplifies the retrofitting of the new sensor device to an existing material working device in advantageous manner to create a material working device as presently disclosed.

In a further embodiment of the present disclosure, the material-working device has a computerised control device which, when the scanner mirrors have coatings with different reflectivities at the sensor wavelength and the laser wavelength, is provided with a deep-pass characteristic which filters a sensor wavelength greater than the laser light wavelength out of a reflected signal reflected off the scanner mirrors and evaluates it for distance measurement.

As an alternative to deep-pass filtering it is also possible to measure a spectral envelope $I_{0\text{-}mean}(k)$ in a calibration run for each combination of galvano mirror orientations. Here a plane face with known spectral reflectivity is measured. For this purpose the material-working device has a computerised control device which initiates calibration runs when the scanner mirrors have coatings with different reflectivity at the sensor wavelength and the laser wavelength. These calibration runs are able to measure and save in tabular form in the computererized control device any combination of orientations of the galvanically coated scanner mirrors relative to a plane face with known spectral reflectivity, the saved table than being taken into account in the evaluation of the reflected measuring signal.

This solution can only be used if the waviness of the reflected measurement signal does not prove too great. This is essentially because it is not possible to separate the term $\exp[i*\Phi(\lambda)]$. Only $[E_1]$ and $[E_2]$ can be determined and eliminated. It is therefore necessary to assume that $\Phi(\lambda)$ lies in the interval $\pm\pi/2$ along the entire wavelength range. It is also conceivable that the mixed term has a node where $[E_R]^*[E_R]=0$ and where the phase of the carrier frequency inverts, i.e., jumps by $\pi$. This can be captured by using a sign change of $[ER]^*[ER]$ when dividing by $[E_R]^*[E_R]$ at the node.

This gives the following:
Generally $$E_0 = E_1(\lambda)*\exp[i*\Phi(\lambda)]$$

with real $E_1$ and thus $$I = |E_R|^2 + |E_1|^2 + 2|E_R|*|E_1|\{\cos\Phi(\lambda)*\cos[4\pi(z_0 - z_R)/\lambda] - \sin\Phi(\lambda)*\sin[4\pi(z_0 - z_R)/\lambda]\}$$

$$= |E_R|^2 + |E_1|^2 + 2|E_R|*|E_R|*\cos[4\pi(z_0 - z_R)\lambda + \Phi(\lambda)]$$

The following spectra are preferably measurable:

$$I_{reference}=E_R^2 \text{(object arm masked)}$$

$$I_{object}=E_1^2 \text{(reference arm masked)}$$

If these are known, it is possible to separate the cosine term from the I which is also measured. The problem is now that the phase distortion cannot simply be separated from the distance phase $$\Phi 0(\lambda)=4\pi(z_0-z_R)/\lambda$$

since they only occur as a sum in $I(\lambda)$. $|E_R|$ and $|E_1|$ are now therefore calculated. The mixed term $$2|E_R|*|E_R|*\cos[4\pi(z_0-z_R)\lambda+\Phi(\lambda)]$$

is then divided by $|E_R|*|E_R|$. The reflection amplitudes are eliminated by comparing the filtered Fourier-transformed Fourier spectra to determine the spectral modulation. The carrier frequency-filtered spectrum is then divided by the spectral modulation to form a weighting operation.

A measurement series with three closely positioned workpiece/plane mirror or reference mirror distances with:

$$I(z_0-\Delta z), I(z_0) \text{ and } I(z_0+\Delta z)$$

works in exactly the same manner.

Subtraction gives:

$$I(z_0)-I(z_0+\Delta z)=2E_R*E^{1*}\{[1-\cos(4\pi\Delta z/\lambda)]*\cos[4\pi(z_0-z_R)/\lambda+\Phi(\lambda)]+\sin(4\pi\Delta z/\lambda)*\sin[4\pi(z_0-z_R)/\lambda+\Phi(\lambda)]\}$$

$$I(z_0)-I(z_0-\Delta z)=2E_R*E_1*\{[1-\cos(4\pi\Delta z/\lambda)]*\cos[4\pi(z_0-z_R)/\lambda+\Phi(\lambda)]+\sin(4\pi\Delta z/\lambda)*\sin[4\pi(z_0-z_R)/\lambda+\Phi(\lambda)]\}$$

and finally $$I(z_0)-I(z_0+\Delta z)-[I(z_0)-I(z_0+\Delta z)]=I(z_0-\Delta z)-I(z_0+\Delta z)=$$
$$4E_R*E_1*\sin(4\pi\Delta z/\lambda)*\sin[4\pi(z_0-z_R)/\lambda+\Phi(\lambda)]$$

and $$I(z_0-\Delta z)+I(z_0+\Delta z)=$$
$$4E_R*E_1*[1-\cos(4\pi\Delta z/\lambda)]*\cos[4\pi(z_0-z_R)/\lambda+\Phi(\lambda)].$$

Sine and cosine are thus known and so the desired $\Phi(\lambda)$ can be separated.

It is also possible to determine $\Phi(\lambda)$ using a Fourier method. For this purpose the complex Fourier transform or FFT of the equalised spectrum is set to zero for negative and small layer thicknesses and inverse Fourier transformed. It is assumed that the Fourier peak to the distance measurement lies outside the zeroed region. The result obtained is:

$$I_1=E_R*E_1(\lambda)*\exp[i*\Phi(\lambda)]*\exp[i4\pi(z_0+z_R)/\lambda].$$

Absolute value generation thus gives:

$$I_2=|I_1|=E_R*E_1(\lambda).$$

In the next inverse FFT only layer thicknesses with small amounts are left. This gives:

$$I_3=E_R^{2*}+E_1(\lambda)^2$$

such that $$0=E_R^4-I_3E_R^2+I_2^2.$$

The result lies in the fact that the values $E_R$, $E_1(\lambda)$ and $\Phi(\lambda)$ can be prepared from one single spectrum, the distance measuring spectrum.

Finally, in the last step:

$I_1$ is multiplied by $1/(E_R*E_1(\lambda))$ and Fourier transformed.

Here it is assumed that $\Phi(\lambda)$ is a fairly smooth function.

In a further embodiment of the present disclosure the sensor device has a free-beam pre-modulator which is connected by an optical fibre both to the sensor light sources and to the sensor beam path. For this purpose the free-beam pre-modulator is configured as an interferometer with two arms and the fibre end of the free-beam pre-modulator is configured to be partially reflective towards the sensor beam path. The free-beam pre-modulator causes a first sub-wave to interfere with a second sub-wave. The first sub-wave is reflected in the longer reference arm of the free-beam pre-modulator and at the fibre end, while the second sub-wave is reflected in the shorter object arm of the free-beam pre-modulator and at the workpiece. Here other spectral modulations advantageously lie outside the measuring range of an evaluation unit. To compensate for total dispersion in the sensor beam path, a glass optical assembly with the same dispersion as the total dispersion in the sensor beam path is provided in the freebeam pre-modulator.

A further embodiment of the present disclosure makes provision for an interferometer instead of a free-beam pre-modulator. The interferometer is arranged in the collimated measuring beams upstream of the point where the working laser beam is coupled into the collimated measuring beams. A reference arm of the interferometer compensates for dispersion. For this purpose the reference arm has the same optical length as the object arm between an interferometer beam splitter and the workpiece.

In addition, in a further embodiment of the present disclosure a further sensor head is provided outside the working zone which measures a reference distance to the workpiece and determines an absolute change in working depth in case of laser ablation or in working height in case of deposition.

The present disclosure is better understood and is discussed below in greater detail with reference to the attached drawings.

Figure 1:
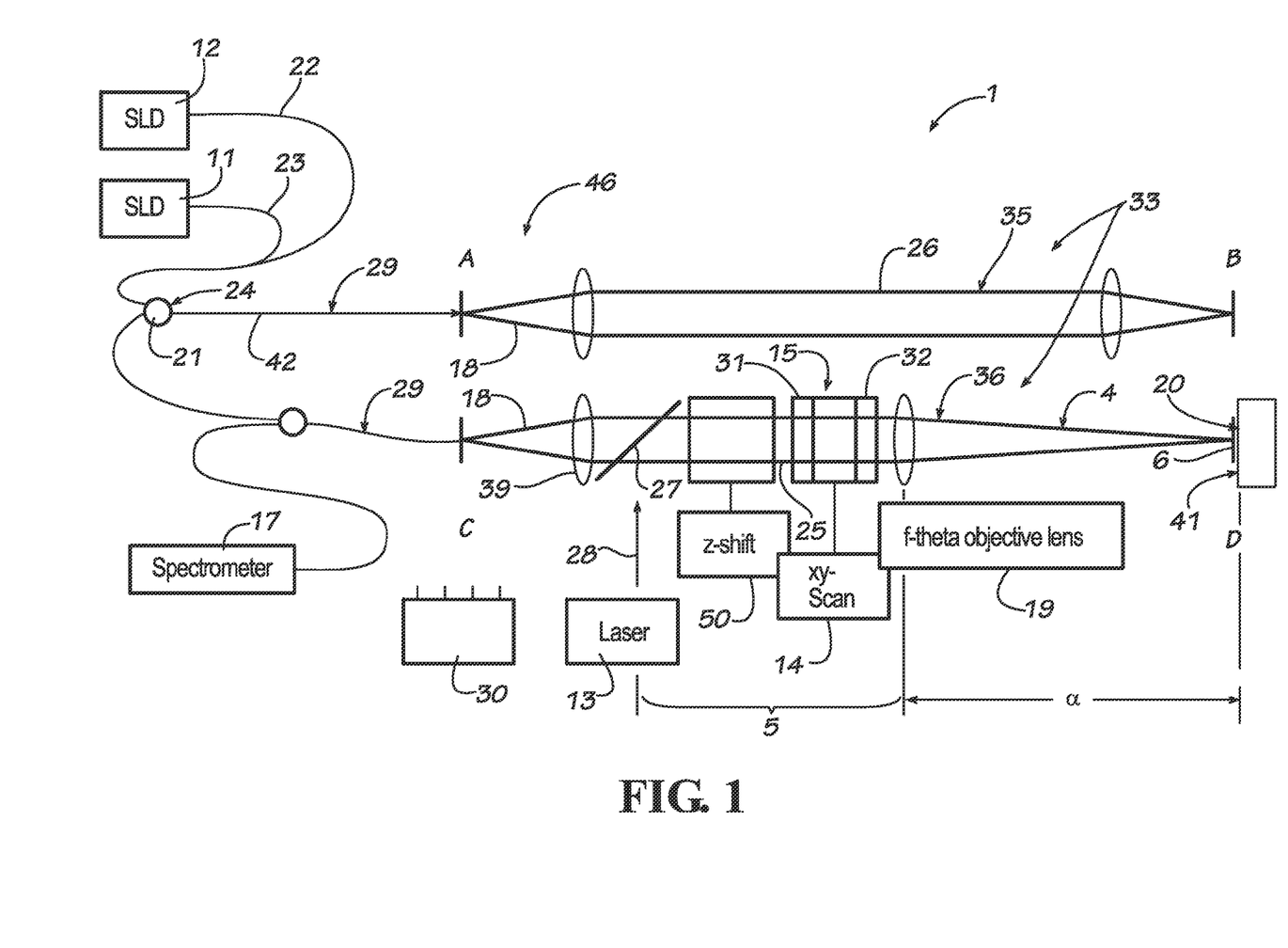
FIG. 1 shows a schematic drawing of a material-working device as disclosed in a first embodiment.

One embodiment of a material-working device is disclosed and described in FIG. 1. FIG. 1 shows a schematic drawing of a material-working device 1 in accordance with a first embodiment. The material-working device 1 works with working beams 4 of a beam generator 5 and with in-situ measurement of the working distance (a) between the beam generator 5 and a workpiece 6. For this purpose the material-working device 1 has a working laser 13 with near-infrared working beams 4. A laser scanner 14 comprising a two-dimensional deflecting device 15 with scanner mirrors 31 and 32 is arranged downstream of a working laser 13. An automatic refocusing device for varying working distances a(t) is provided in the form of a Z-shift device 50. As such, this device can act as a variable refocusing device for varying working distances, that is to say, to vary the distance that the beam generator or laser scanner is from the workpiece. A similar variable refocusing device 50 is shown in FIG. 2.

A sensor device 16 comprising a spectrometer 17 and sensor light sources 11 and 12 generates measuring beams 18 which jointly sense the working area 20 of the workpiece 6 by means of the laser scanner 14 and an objective lens 19 while recording the workpiece distance a. The measuring beams 18 of 30 the sensor light sources 11, 12 are linearly polarised and coupled by means of an optical coupling element 21 into the working beam path 25 of the laser scanner 14 of the material-working device 1 with crossed polarisation directions in a collimated state. The light sources 11 and 12 are formed by two superluminescent diodes (SLDs) with linearly polarised beams. These light sources 11 and 12 are connected by polarisation-maintaining optical fibres 22 and 23 to a polarisation beam coupler or coupling element 21 which combines the crossed polarisation directions by means of a polarising beam splitter 24 to form a sensor light 29 in an optical fibre 42 and forms the measuring beams 18 of the sensor beam path 26.

The material-working device 1 has a computerised control device 30 which, when the scanner mirrors (31, 32) have coatings with different reflectivities at the sensor wavelength and the laser wavelength, is provided with a deep pass characteristic which filters a sensor light wavelength greater than the laser light wavelength out of the reflected signal and evaluates it for the distance measurement. When the scanner mirrors (31, 32) have coatings with different reflectivities at the sensor wavelength and the laser wavelength, the computerised control device 30 triggers calibration runs with which each combination of orientations of the galvanically coated scanner mirrors 31, 32 compared to a plane surface with known spectral reflectivity is measured and saved in tabular form in the computererized control device, the saved table being taken into account when evaluating the reflected measurement signal.

Figure 2:
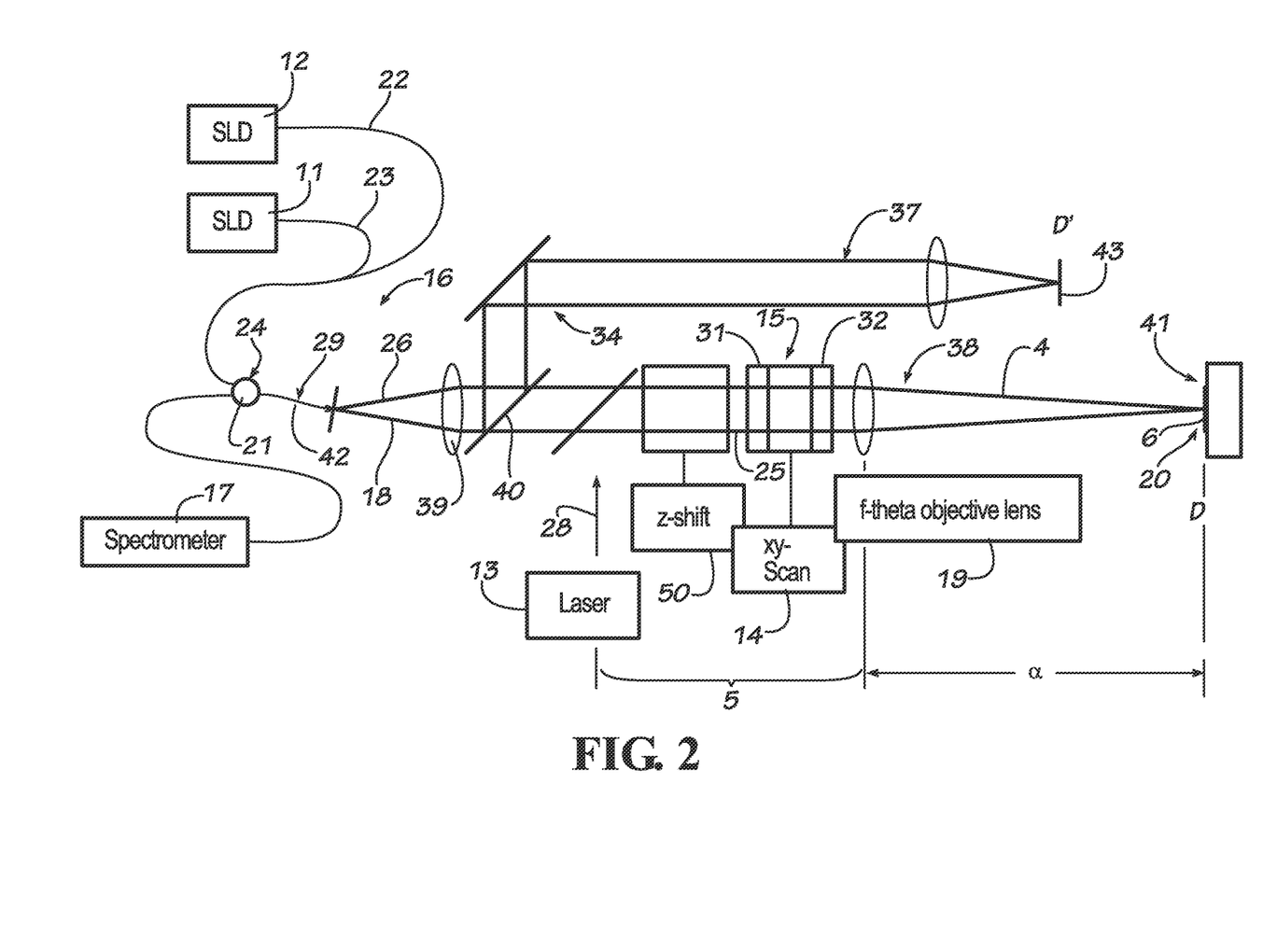
FIG. 2 shows a schematic drawing of a material-working device in accordance a second embodiment.

For both the material-working device 1 as disclosed in FIG. 1 and the material-working device 2 as disclosed in FIG. 2, the laser scanner optical assembly preferably consists of the following components:

1. a beam expander 39 with beam convergence control for an axial focus position;
2. a beam splitter for a camera module (not shown in FIGS. 1 and 2) for observing the working area 20 which is typically designed for 650 nm;
3. a pair of galvano mirrors 31 and 32 for deflecting the collimated beam in x and y directions which are oriented orthogonally in relation to the optical z-axis;
4. an F-theta objective lens system which is a special objective lens 19 for use together with the galvanically coated pair of galvano mirrors 31 and 32 and is preferably telecentric for focusing the collimated working beam 4 in the working plane 41, i.e., the focused working beam 4 strikes the surface perpendicularly everywhere in the measuring/working field.

The Numerical Aperture (NA) of the focussed beam 4 typically lies under 0.1 with a beam cone under +/−5°. Once the surface inclination exceeds the cone angle, no light is mirrored back into the "coaxial" sensor device 16 in which the direction of lighting is identical to the direction of detection. As a result, optical sensors which are also able to evaluate stray light from inclined surfaces are used in the spectrometer 17. As the surface is generally roughened by laser processing, stray light can be expected and an evaluatable component is therefore reflected from the workpiece 6 in detection direction.

Confocal chromatic sensors have proved unsuitable in this arrangement because the low Numeric Aperture of the scanner optical assembly leads to a high level of measurement inaccuracy. A further disadvantage of such confocal chromatic sensors is the temperature-dependent calibration curve which means that the heating of the f-theta lenses due to the working laser can modify the characteristic curve of the confocal chromatic sensors.

FIGS. 1 and 2 use unpolarised light sources 11 and 12, namely two superluminescent diodes (SLDs) but with linearly polarised beams, which are carried by polarisation-maintaining optical fibres 22 and 23 to a PBC (Polarisation Beam Combiner) and combined with crossed polarisation directions by a polarising beam splitter 24 in the PBC.

Optical components such as beam splitters and galvano mirrors with different spectral transmissions depending on direction of polarisation prevent the polarisation state and thus the mix ratio between polarisation modes and so the spectral transmission from being modified by shaking at the optical fibres 22, 23 or 42. If, however, there are different path differences in the two directions of polarisation (due to stress-induced birefringence or coating, for example), the distance peak splits into two sub-peaks. To separate the two sub-peaks to such an extent that a clean evaluation is possible, the present disclosure provides for the insertion into the beam path of a birefringent element with main directions which correspond to the main directions of the polarisation-relevant components such as a beam splitters and galvano mirrors.

Spectral optical FD (OCT) (Fourier Domain Optical Coherence Tomography) sensors are used in the embodiments of the present disclosure shown in FIGS. 1 and 2. However, they have the following disadvantages which can be overcome by means of the subject matter of this disclosure.

Uncontrolled path changes between object- and reference-arm due to temperature drift or shaking at the optical fibres is compensated for in the present disclosure by the use of at least two light sources.

Clearly different intensities from the object and reference arms and thus low spectral modulation depth caused for example by the inclined surface and/or by defocusing are compensated for in the present disclosure by minimal measuring spot diameter.

Defocusing on rough surfaces reduces measuring quality since, in contrast to the mirroring surface which returns only one sub-beam bundle to the optical fibres, each lit part of the rough surface brings stray light towards the optical fibres. An optical fibre thus sees "a mixture of distances". This also fringes out the Fourier peak. The smaller the spot on a rough surface, the greater the "speckies" from stray light. For this reason a minimal measuring spot diameter is advantageously generated with a focus on the surface in the present disclosure.

Poor transmission of sensor light through the beam path of the scanner optical assembly is avoided by ensuring that the sensor wavelength does not deviate significantly from the laser wavelength. To achieve this, the coating of optical components of the scanner optical assembly is adjusted to the laser wavelength. This applies in particular to all anti-reflex, mirror or beam splitter layers.

Spectral transmission which can be modified dependent on the angle of tilt of the galvano mirrors thanks to dielectric mirror layers for a wavelength area, particularly since bare metal mirrors are not suitable for laser light, is almost neutralised by the measures disclosed herein. The dependence of optical path differences on temperature and vibrations can be eliminated by the provision of an environmentally resistant reference wave. In FIG. 1 a premodulator 33 is used for this purpose which is connected both to the light sources 11 and 12 and to the sensor beam path 26 by an optical fibre 42 and is configured as an interferometer with two arms points A and B. The fibre end point C is configured to be partially reflective towards the sensor beam path 26. Light from the sensor light sources is divided in the interferometer to form sub-waves. The sub-wave which is reflected in the longer reference arm 35 (point B) of the pre-modulator 33 and at the fibre end point C is made to interfere with the sub-wave which is reflected in the shorter object arm 36 (point A) and at the workpiece 6 (point D). The other interferences between subwaves have such great path differences that their spectral modulation is no longer resolved by an FD OCT sensor or lies outside the measuring range of a TD OCT sensor.

The optical path length in the sensor beam path 26 as far as the workpiece surface is dependent on wavelength because the glass components have dispersions. Located in the reference arm of the free-beam pre-modulator 33 are glass components with the same total dispersion as the object arm. For this reason a glass optical assembly with the same optical dispersion as in the sensor beam path from point C to point D is provided for the free-beam pre-modulator 33.

FIG. 2 shows a schematic drawing of a material-working device 2 in accordance with a second embodiment. Components with the same functions as in FIG. 1 are indicated by means of the same reference numerals and are not discussed in further detail here. In FIG. 2 instead of the free-beam pre-modulator an interferometer 34 is used in the collimated measuring beams upstream of the point where the beam is coupled into the working beam path 25, the reference arm 37 having a dispersion-compensating effect and being of approximately the same length as the object arm 38 from the interferometer-beam splitter 40 to the workpiece 6.

By means of controllable diaphragms and/or filters it is possible to adjust the brightness of the light wave in the reference arm 37. Diaphragms or filters with constant spectral transmission, a constant optical path and no dispersion effects or wavefront aberrations are preferably used for this purpose.

One preferred embodiment is a reference mirror 43 with spatially variable reflectivity which can be pushed along the mirror plane such that the spot of the sensor light which strikes the reference mirror 43 focused is varied in intensity. It is also possible to use devices which modify spectral transmission or path length in a predictable manner such that they can be taken account by the evaluation software.

The three-dimensional sensor spot position can be calibrated with a planar mirroring calibration body which is marked with a raster and can be height-adjusted. The f-theta objective lens system 19 has image field curvature and distortion. In addition, the optical path length of the sensor beam—plotted over the field of view in x- and y-directions—is saddleshaped as far as the workpiece plane 41. For this reason in the present disclosure, a calibration run determines the relationship between the scanner mirror angles and the setting of a focus adjuster on one hand and the three-dimensional position of the spot, its optical path as measured by the sensor and its defocusing on the other.

A reference mirror which can be moved approximately half a sensor centre wavelength in z-direction in a plurality of defined steps is used for phase-shifting measurement. A position-controlled piezo-actuator or a transverse oscillating stepped mirror can be used for this purpose. For a phase-shifting measurement a sequence of at least three spectra with, for example, equidistant steps j=1, 2, 3 is measured. This gives:

$$I(j) = I(z_0 + j*f\Delta z)$$
$$= E_R^2 + E_1^2 + 2E_R*E_1*\{\cos(4\pi j*\Delta z/\lambda)*\cos[4n(z_0-z_R)/\lambda+\Phi(\lambda)] - \sin(4\lambda j*\Delta z/\lambda)*\sin[4\pi(z_0-z_R)/\lambda+\Phi(\lambda)]\}$$

Figure 3A:
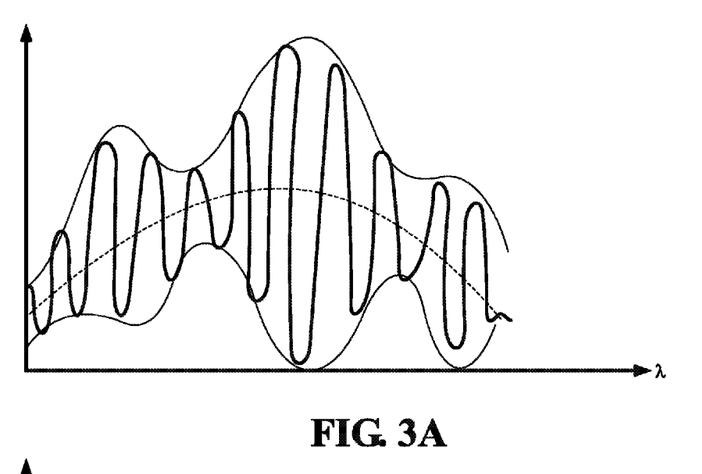
Figure 3B:
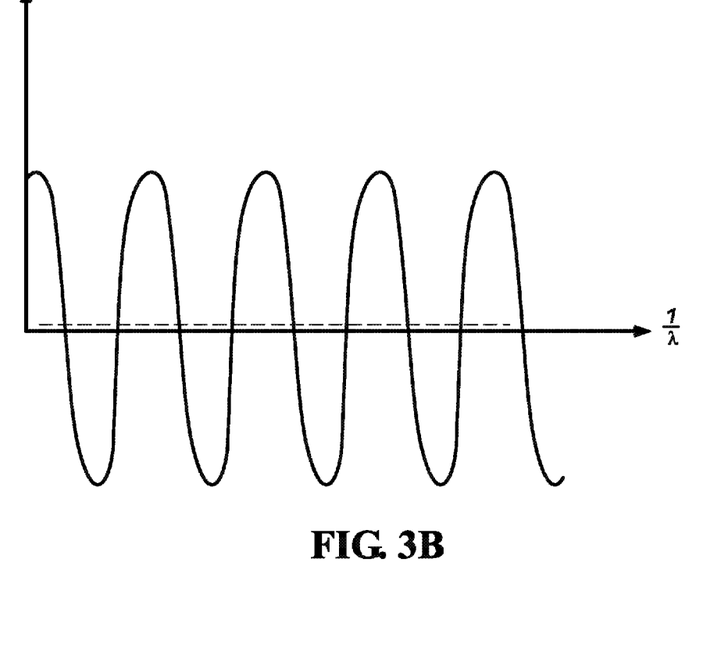

When evaluating the measurement the phase value is calculated for each k-pixel, the known terms $\cos(4\pi j*\Delta z/\lambda)$ and $\sin(4\pi j*\Delta z/\lambda)$ being used to determine the phase $[4\pi(z_0-z_R)/\lambda+\Phi(\lambda)]$. The purpose of the phase-shifting measurement is to achieve a more robust measurement value as a result of the higher number of measurements used in the evaluation. FIG. 3 shows a raw spectrum (FIG. 3a) and a leveled spectrum (FIG. 3b) after working as disclosed herein. The raw spectrum has the shape of the diagram shown in FIG. 3a. The broken line is measured without light from the object (reference light only). In the spectrum equalised to $k=1/\lambda$ the reference light is subtracted, giving $I_0(k)$. The spectral envelope $I_{0mean}(k)$ is calculated and divided using a deep-pass filter to obtain a spectral modulation with constant amplitude in FIG. 3b. Finally, an FFT is carried out.

Figure 4:
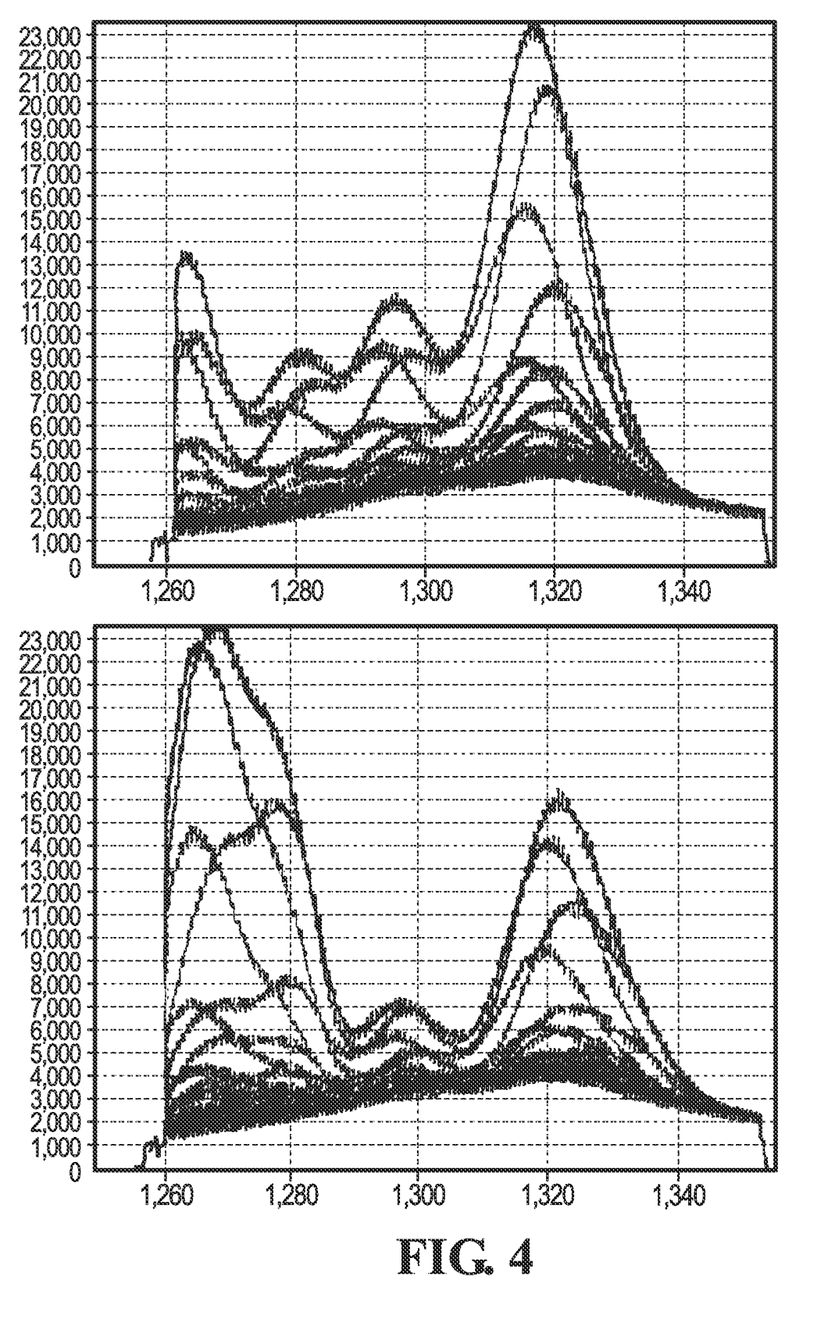
FIG. 4 shows two measured reflection spectra of a plane mirror of a laser scanner.

FIG. 4 shows two measured reflection spectra of a plane mirror of a laser scanner in the spectral range 1260 to 1360 nm and two angled positions of the galvano mirror pair. Each diagram shows a plurality of spectra during refocusing in equidistant steps. They show that during refocusing the focus of intensity moves from the shorter-wave side to the longer-wave side of the spectrum. Moreover, the spectral envelope has a wavy shape which is different in the two mirror positions. The waviness is created by a dielectric mirror layer of the galvano mirror.

Figure 5A:
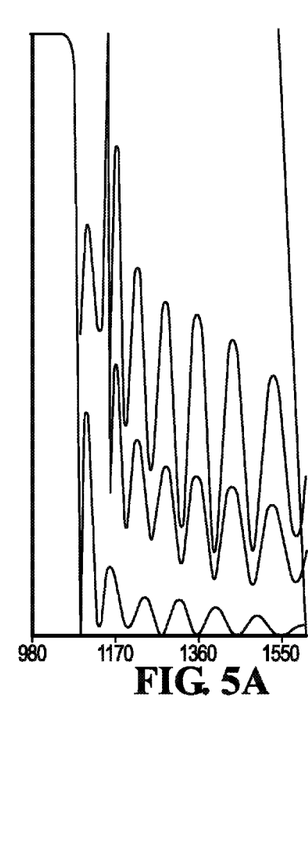
Figure 5B:
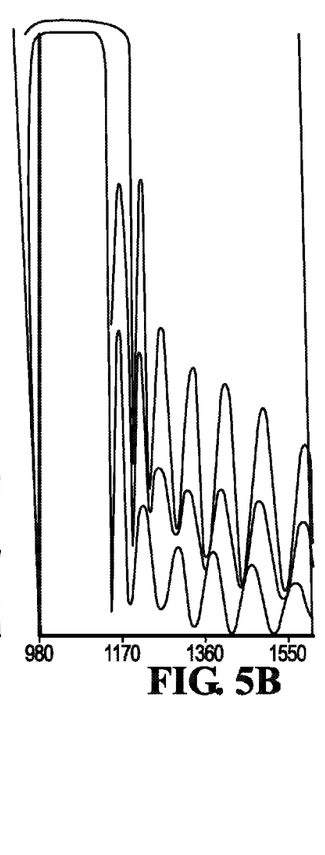
Figure 5C:
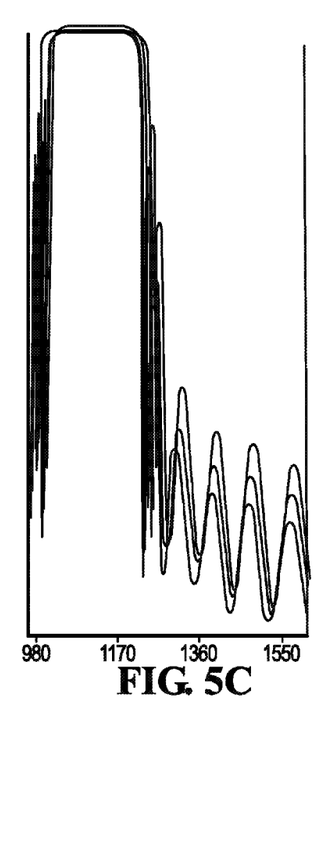

FIG. 5 shows polarisation- and angle-dependent transmission of the scanner mirrors 31 and 32 used. FIG. 5 shows the polarisation-dependent reflection spectrum of a single galvano mirror for three angles of incidence, namely for an angle of incidence of 57.5° in FIG. 5a, an angle of incidence of 45° in FIG. 5b and an angle of incidence of 27.5° in FIG. 5c. Dotted curves represent s-polarisation, dashed curves represent ppolarisation and continuous curves represent "random polarisation".

In the 1050 nm laser wavelength range is a broad plateau with high, polarisation-dependent reflectivity which rises towards the short wavelength as the angle of incidence increases. At high wavelengths reflectivity is weak and spectrally modulated, in some cases falling to R<1% ein. Modulation is almost counter-phase in both polarisation directions. Because one pair of mirrors is always working in the structure, total reflectivity is even more complex. Given the scanner geometry, a wave which strikes the first mirror p-polarised, necessarily strikes the second s-polarised and vice versa.

The spectral waviness of the mirror reflectivity and the beat phenomena in the reflection spectrum of the total structure show that the galvano mirror has a plurality of very thin "natural layer thicknesses" which are also measured by the spectral interferometer. The distance measurement therefore measures not one single Fourier peak but the overlapping of a plurality of sub-peaks. The distance and weighting of the sub-peak depend on the mirror angles and on the polarisation state.

Seen mathematically, the object wave and the reference wave have the following shape:

$$E_{object} = E_0*\exp[i*4\pi z0/\lambda]$$

$$E_{reference} = E_R*\exp[i*4\pi z_R/\lambda]$$

Here $z_0$ and $z_R$ are the migration distances in the two interferometer arms. In the undistorted case $E_0$ and $E_R$ are constants. The measured intensity $$I = \{E_{object} + E_{reference}\}\{E^*_{object} + E^*_{reference}\}$$
$$= I_{object} + I_{reference} + I_{mod}$$

contains the interference term $$I_{mod} = (E_0*E^*_R + E^*_0*E_R)*\cos[4\pi(z_0-z_R)/\lambda]$$

from which the path difference of the arms is determined. In the undistorted case the pre-exponential factor becomes 2 $E_0*E_R$. Due to the reflectivity of the galvano mirrors the object wave presents complex modulation. Two natural layer thicknesses d1 and d2 are applied by way of example:

$$E_0 = E_1 * \exp[i*4\pi d_1/\lambda] + E_2 * \exp[i*4\pi d_2/\lambda]$$

resulting in:

$$I_{object} = |E_1|^2 + |E_2|^2 + 2|E_1|*|E_2|*\cos[4\pi(d_1-d_2)/\lambda]$$

$$I_{mod} = (E_1 * E_R + E_1^* * E_R)*\cos[4\pi(z_0 + d_1 - z_R)/\lambda] +$$

$$(E_2 * E_R^* + E_2^* * E_R)*\cos[4\pi(z_0 + d_2 - z_R)/\lambda]$$

$$= (E_1 * E_R^* + E_1^* * E_R)$$

$$\{\cos[4\pi d_i/\lambda]*\cos[4\pi(z_0 Z_R/\lambda] - \sin[4\pi d_1/\lambda]*$$

$$\sin[4\pi(z_0 - z_R)/\lambda]\} +$$

$$(E_2 * E_R^* + E_2^* * E_R)*$$

$$\{\cos[4\pi d_2/\lambda]*\cos[4\pi(z_0 - z_R)/\lambda] - \sin[4\pi d_2/\lambda]*$$

$$\sin[4\pi(z_0 - z_R)/\lambda]\}$$

$$= \{(E_1 * E_R^* + E_1^* * E_R)\cos[4\pi d_i/\lambda] +$$

$$(E_2 * E_R^* + E_2^* * E_R)\cos[4\pi d_2/\lambda]*\cos[4\pi(z_0 - z_R)/\lambda] -$$

$$(E_1 * E_R^* + E_1^* * E_R)\sin[4\pi d_i/\lambda] +$$

$$(E_2 * E_R^* + E_2^* * E_R)\sin[4\pi d_2/\lambda]*\sin[4\pi(z_0 - z_R)/\lambda]\}$$

As applied, the spectrum accordingly contains two closely positioned layer thicknesses and forms beating phenomena.

Figure 6:
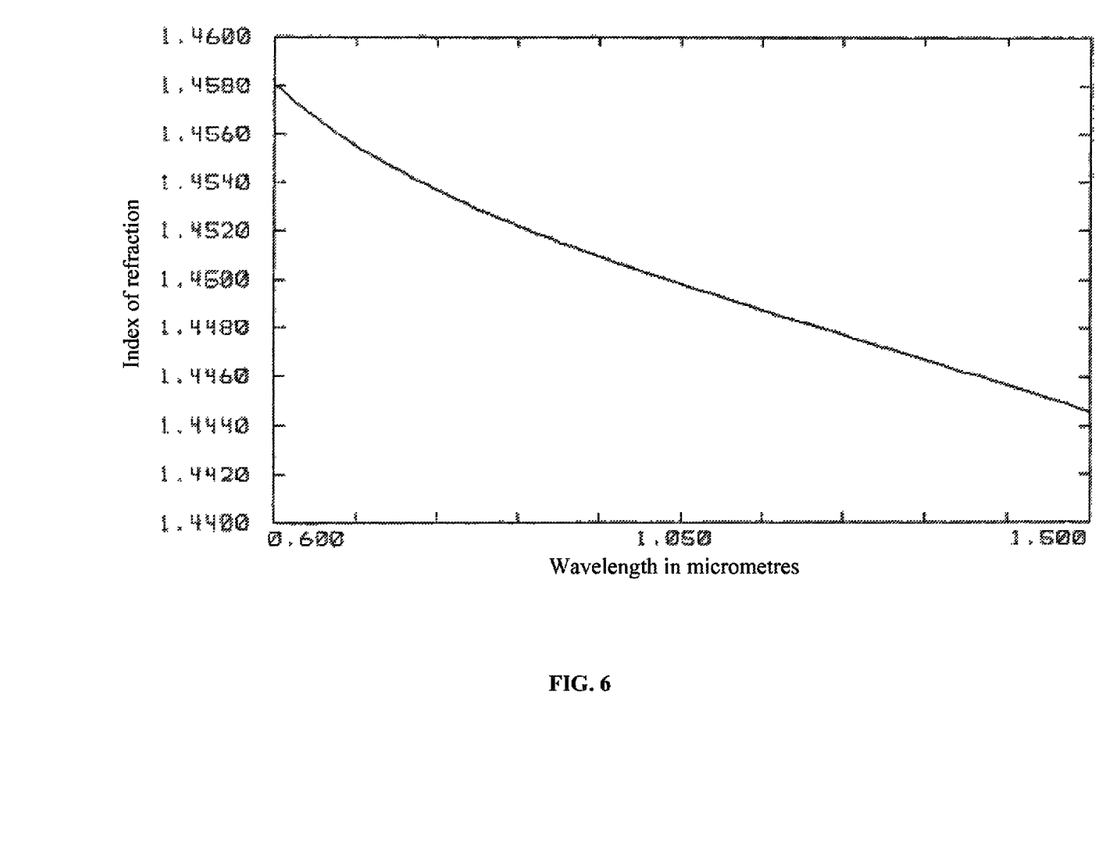
FIG. 6 shows the index of refraction of quartz glass in the vicinity of laser wavelengths of approx. 1050 nm.

FIG. 6 shows the index of refraction of quartz glass in the vicinity of laser wavelengths of approximately 1050 nm. This wavelength-dependent index of refraction of quartz glass can be used for extended depth of field by employing chromatic focal spot displacement. The f-theta objective lens systems are not generally achromatic as they are designed for individual laser wavelengths. However, achromasia is difficult to achieve because types of glass which are resistant to the high peak intensities of pulse lasers such as quartz glass are preferred.

The focal length f is therefore wavelength-dependent when using quartz glass. According to the formula for a thin plane convex lens with a radius of curvature R, in general terms $$1/f = [n(\lambda) - 1]/R.$$

Thus: $f = f_0/[1+(n(\lambda)-n_0)/(n_0-1)]$ $f_0$ and $n_0$ being the focal length and index of refraction at the laser wavelength.

With Taylor development this gives:

$$f \approx f_0 - f_0 \Delta n/(n_0 - 1)$$

For a quartz lens with f=100 mm the spectral index of refraction shift is 1.2e-5/nm and the focal spot shift is thus 2.7 pm/nm. At a sensor bandwidth of 100 nm the focal spot shift in the spectrum is already 270 pm. This is contrasted by the depth of field range which is set by the Rayleigh length at which the beam cross-sectional area of a Gaussian beam—based on the beam focus—doubles (or intensity halves)

$$z_R = \pi w_0^2 / \lambda.$$

Here $w_0$ is the beam radius in the focus at which the intensity dropped to e-2=0.135 of the middle intensity. In relation to the Numerical Aperture (NA):

$$w_0 = \lambda/[\pi \tan(\arcsin NA)].$$

With the paraxial approximation $NA = \lambda/nw0$ this results in:

$$z_R = \lambda/(\pi NA^2).$$

For a NA=0.05 and 1050 nm wavelength therefore: $w_0 = 13$ μm and $z_R = 133$ pm.

Figure 7:
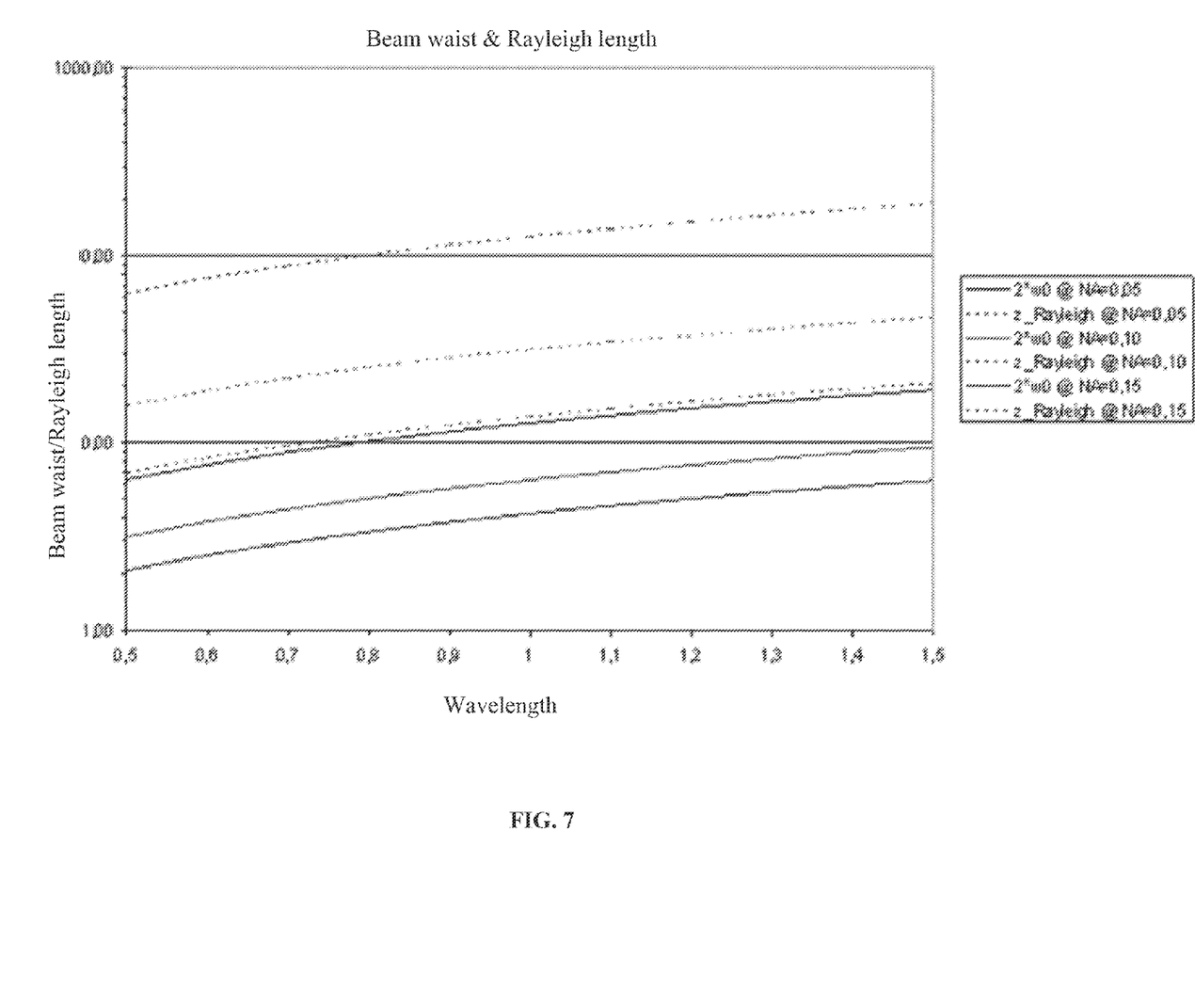
FIG. 7 shows a diagram for Gaussian beam parameters in relation to beam waist diameter and Rayleigh length.

FIG. 7 shows a diagram for Gaussian beam parameters in relation to beam waist diameter and Rayleigh length. The focal spot shift for 100 mm focal length and 100 nm bandwidth calculated above was 270 pm and is twice as big. As a result at NA=0.05 the edge wavelengths of the sensor spectrum are weakened by a factor of 0.5 by defocusing.

The measurements in FIG. 4 were carried out at approximately NA=0.10. Here the weakening of the defocused wavelengths is even more extreme because $z_R = 33$ μm. At $w_0 = 6.6$ μm the spot diameter is only half as big. This is favourable for the quality of the distance measurement in the focus. However, the stronger weakening during defocusing is disadvantageous.

The chromatic focal spot shift of the f-theta lens is used to simultaneously obtain a small spot at high NA and a large capture range for a focused measurement. In the example this is 270 pm for a 100 nm sensor bandwidth. If the workpiece is located in the capture range, a wavelength reaches maximum sharpness in the sensor band. Only wavelengths around the focus maximum with focal spot displacement <+/−$z_R$ make a notable contribution to the signal. For this reason the following measures are taken:

1. When the spectrum is equalised and standardised the window function selected is significantly narrower than the sensor bandwidth and whose maximum lies in the intensity maximum of the raw spectrum.
2. In a "passive" variant there is no windowing at all as this is already achieved physically by wavelength-dependent defocusing.
3. To roughly localise the workpiece a sensor with a large capture range, that is an extremely broad-band sensor, is used. Here the measurement process can be either spectrally interferometric or chromatically confocal. A series of narrow-band spectrally interferometric sensors are responsible for the fine measurement. Their wavelength ranges overlap and together cover the spectrum of the rough sensor. One of these sensors is activated at a time.
4. A multisensory concept of this type takes the form of a single spectrometer. A spectrometer with an echelle grating which detects various spectral ranges dependent on diffraction order is used for this purpose. Here a plurality of SLD light sources is used, each SLD being allocated a specific diffraction order. Fibre couplers, fibre circulators and/or WDM couplers, a fibre analogon to the dichroic beam splitter, or alternatively a free-beam coupler, are provided to connect the SLDs to the measuring head and the spectrometer. The fibre channels towards the interferometer are coupled by a fibre switch to an end fibre (so that measurements are always taken at the same point). The fibres towards the spectrometer are combined to form an array perpendicular to the direction of spectral diversification. The pixels in the line detector in array direction are long enough (0.5 or 1 mm) to capture the light from any fibre in the array.

FIG. 8 shows a partially perspective principle drawing of a material-working device in accordance with the prior art which has already been discussed in the introduction and which does not therefore require further consideration at this point. The material-working device 1 has a computerised control device which, where the scanner mirrors 31 and 32 have coatings with different reflectivity at the sensor wavelength and the laser wavelength, is equipped with a deep-pass characteristic that filters a sensor light wavelength which is greater than the laser light wavelength out of the reflected signal and evaluates it for the distance measurement. Where the scanner mirrors 31 and 32 have coatings with different reflectivity at the sensor wavelength and the laser wavelength, the computerised control device 30 triggers calibration runs with which each combination of the orientations of the galvanically coated scanner mirrors 31 and 32 is measured in comparison to a plane surface with known spectral reflectivity and stored in tabular form in the computererized control device, the stored table being taken into account in the evaluation of the reflected measurement signal.

LIST OF REFERENCE NUMERALS

1 Material-working device (first embodiment)
2 Material-working device (second embodiment)
3 Material-working device (prior art)
4 Working beam
5 Beam generator
6 Workpiece
7 Working head
8 Industrial robot
9 Curve
10 Tomograph
11 First light source
12 Second light source
13 Working laser
14 Laser scanner
15 Deflecting device
16 Sensor device
17 Spectrometer
18 Measuring beam
19 Objective lens
20 Working area
21 Optical coupling element
22 Optical fibre
23 Optical fibre
24 Beam splitter
25 Working beam path
26 Sensor beam path
29 Sensor light
30 Control device
31 Scanner mirror
32 Scanner mirror
33 Free-beam pre-modulator
34 Interferometer
35 Reference arm of the free-beam pre-modulator
36 Object arm of the free-beam pre-modulator
37 Reference arm of the interferometer
38 Object arm of the interferometer
39 Beam expander
40 Interferometer beam splitter
41 Working plane
42 Optical fibre
43 Reference mirror
A Direction of arrow
a Distance One should note that conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment. It should be emphasized that the above-described embodiments are merely possible examples of implementations, merely set forth for a clear understanding of the principles of the present disclosure. Any process descriptions or blocks in flow diagrams should be understood as representing modules, segments, or portions of code which include one or more executable instructions for implementing specific logical functions or steps in the process, and alternate implementations are included in which functions may not be included or executed at all, may be executed out of order from that shown or discussed, including substantially concurrently or in reverse order, depending on the functionality involved, as would be understood by those reasonably skilled in the art of the present disclosure. Many variations and modifications may be made to the above-described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

The which is claimed is:

1. A material-working device with working beams of a beam generator and with in-situ measurement of a working distance between the beam generator and a workpiece, the material-working device comprising:
a working laser;
a laser scanner for the working laser, the laser scanner including a two-dimensional deflecting device with scanner mirrors and a variable refocusing device for varying working distances;
an objective lens; and
a sensor device including a spectrometer, at least two sensor light sources generating measuring beams, and an optical coupling element,
wherein the measuring beams are linearly polarized in crossed polarization directions and collimated using the optical coupling element, and then directed to the workpiece through the laser scanner and the objective lens, and then directed back to the spectrometer to record the workpiece distance.

2. The material-working device according to claim 1, wherein the light sources include superluminescent diodes with linearly polarized beams, and the linearly polarized beams are directed by polarization-maintaining optical fibers to the optical coupling element, wherein the optical coupling element includes a polarizing beam splitter which combines the linearly polarized beams in the crossed polarization directions.

3. The material-working device according to claim 1, wherein the measuring beams define a sensor beam path and the optical coupling element includes a narrow-band dichroic beam splitter to couple the measuring beams into the working beam path in a collimated state.

4. The material-working device according to claim 1, wherein the measuring beams define a sensor beam path and the optical coupling element includes a narrow-band notch filter to couple the measuring beams into the working beam path in a collimated state.

5. The material-working device according to claim 1, wherein the optical element includes a rotating filter wheel which coupling alternately couples at least one of laser light and sensor light into the laser scanner and rotates synchronously with a pulse frequency of the working laser such that the laser scanner is made available for the measuring beam in pulse pauses, the rotating filter wheel coupling the combined measuring beams into the working beam path.

6. The material-working device according to claim 1, wherein the optical coupling element includes a deflecting mirror that is pivotable into the working beam path, and wherein the combined measuring beams may be coupled into the working beam path in a collimated state by pivoting the deflecting mirror.

7. The material-working device according to claim 1, wherein each sensor light source includes a sensor wavelength, the sensor wavelength capable of being set within a camera window wavelength range of the scanner mirrors.

8. The material-working device according to claim 1, wherein the scanner mirrors have coatings which have substantially identical reflectivity at a sensor wavelength and a laser wavelength.

9. The material-working device according to claim 1, wherein the scanner mirrors include coatings with different reflectivities at a wavelength of the measuring beams and a wavelength of a laser light from the working laser, wherein the material-working device includes a computerized control device provided with a deep-pass filter that filters sensor light at a wavelength greater than the wavelength of laser light out of a reflected signal reflected from the workpiece and evaluates it for distance measurement from the beam generator to the workpiece.

10. The material-working device according to claim 1, wherein the scanner mirrors include coatings with different reflectivities at a wavelength of the measuring beams and a wavelength of a laser light from the working laser, and wherein the material-working device includes a computerized control device that triggers calibration runs which measure and save in a table in the computerized control device each combination of orientations of the coated scanner mirrors relative to a plane surface with known spectral reflectivity, the table being taken into account when evaluating a reflected sensor signal.

11. The material-working device according to claim 1, wherein the sensor device includes a free-beam pre-modulator which is connected by an optical fiber to both the sensor light sources and a sensor beam path defined by the measuring beams.

12. The material-working device according to claim 11, wherein the free-beam pre-modulator is configured as an interferometer with two arms.

13. The material-working device according to claim 12, wherein the free-beam pre-modulator includes a fiber end configured such that it is partially reflective towards a sensor beam path defined by the measuring beams.

14. The material-working device according to claim 11, further comprising an interferometer, wherein light from the sensor light sources is divided in the interferometer to form sub-waves, and wherein a first sub-wave is made to interfere with a second sub-wave, the first sub-wave being reflected in a longer reference arm of the free-beam pre-modulator at a fiber end of the free-beam pre-modulator and the second sub-wave being reflected in a shorter object arm at the workpiece.

15. The material-working device according to claim 11, wherein a glass optical assembly with dispersion identical to the total dispersion in a sensor beam path defined by the measuring beams is arranged in the free-beam pre-modulator.

16. The material-working device according to claim 11, wherein said device includes a point where the working laser beam is coupled into the collimated measuring beams and an interferometer is arranged in the collimated measuring beams upstream of the point where the working laser beam is coupled into the collimated measuring beams, said interferometer having a reference arm, an object arm and an interferometer beam splitter, said reference arm of the interferometer having a dispersion-compensating effect and the reference arm having the same optical length as the object arm between the interferometer beam splitter and the workpiece.

17. The material-working device according to claim 11, there being arranged outside the working area a second sensor head which records a reference distance to the workpiece and determines an absolute change in working depth during laser ablation or in working height during material deposition.

* * * * *